(12) United States Patent
Fan et al.

(10) Patent No.: US 9,707,171 B2
(45) Date of Patent: Jul. 18, 2017

(54) ANTIPERSPIRANT/DEODORANT WITH ALKYLATED POLYVINYLPYRROLIDONE

(71) Applicant: Colgate-Palmolive Company, New York, NY (US)

(72) Inventors: Aixing Fan, Bridgewater, NJ (US); Jeffrey Mastrull, Middlesex, NJ (US); Claudio Ortiz, Dayton, NJ (US); Nadia Soliman, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/649,954

(22) PCT Filed: Dec. 11, 2012

(86) PCT No.: PCT/US2012/068903
§ 371 (c)(1),
(2) Date: Jun. 5, 2015

(87) PCT Pub. No.: WO2014/092688
PCT Pub. Date: Jun. 19, 2014

(65) Prior Publication Data
US 2015/0290111 A1 Oct. 15, 2015

(51) Int. Cl.
*A61K 8/28* (2006.01)
*A61K 8/18* (2006.01)
*A61K 8/26* (2006.01)
*A61K 8/81* (2006.01)
*A61Q 15/00* (2006.01)

(52) U.S. Cl.
CPC .............. *A61K 8/8176* (2013.01); *A61K 8/26* (2013.01); *A61Q 15/00* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 4,640,709 A * | 2/1987 | Beestman | 504/300 |
| 5,508,024 A | 4/1996 | Tranner | |
| 5,575,990 A * | 11/1996 | Benfatto | A61K 8/062 424/65 |
| 5,843,881 A | 12/1998 | Dubois et al. | |
| 6,180,127 B1 | 1/2001 | Calton et al. | |
| 6,375,937 B1 | 4/2002 | Chopra et al. | |
| 6,503,491 B2 | 1/2003 | Guenin et al. | |
| 6,960,338 B2 | 11/2005 | Li et al. | |
| 7,074,394 B2 | 7/2006 | Li et al. | |
| 7,105,691 B2 | 9/2006 | Holerca et al. | |
| 7,976,828 B2 | 7/2011 | Popoff et al. | |
| 8,053,405 B2 | 11/2011 | Narayanan et al. | |
| 2003/0194416 A1 | 10/2003 | Shefer et al. | |
| 2003/0195133 A1 | 10/2003 | Shefer et al. | |
| 2003/0198652 A1 | 10/2003 | Shefer et al. | |
| 2003/0199402 A1 | 10/2003 | Triplett et al. | |
| 2004/0109833 A1 | 6/2004 | Tang et al. | |
| 2004/0175404 A1 | 9/2004 | Shefer et al. | |
| 2004/0198998 A1 | 10/2004 | Holerca et al. | |
| 2005/0031660 A1 | 2/2005 | Deckner | |
| 2006/0193812 A1 | 8/2006 | Holzner et al. | |
| 2006/0204463 A1 | 9/2006 | Tang et al. | |
| 2006/0263402 A1 | 11/2006 | Deckner et al. | |
| 2006/0292098 A1 * | 12/2006 | Scavone et al. | A61K 8/046 424/66 |
| 2008/0187503 A1 | 8/2008 | Popoff et al. | |
| 2008/0187504 A1 | 8/2008 | Fan et al. | |
| 2008/0187562 A1 | 8/2008 | Fan et al. | |
| 2008/0206164 A1 | 8/2008 | Rollat-Corvol et al. | |
| 2013/0039961 A1 * | 2/2013 | Gonzales | A61K 8/8117 424/401 |
| 2014/0205555 A1 | 7/2014 | Gale et al. | |

FOREIGN PATENT DOCUMENTS

| | | |
|---|---|---|
| EP | 0165227 | 8/1988 |
| EP | 0384034 | 8/1990 |
| JP | S62-114909 | 5/1987 |
| JP | H02-180267 | 7/1990 |
| WO | WO 2005/034897 | 4/2005 |
| WO | WO 2012/120366 | 9/2012 |

OTHER PUBLICATIONS

International Search Report and Written Opinion International Application No. PCT/US2012/068903, mailed Sep. 11, 2013.
ISP, 2008, "Ganex® P-904LC Safety Data Sheet (91/155/EEC)".
Written Opinion in International Application No. PCT/US2012/068903, mailed Nov. 11, 2014.

* cited by examiner

Primary Examiner — Jeffrey T Palenik

(57) ABSTRACT

An antiperspirant/deodorant liquid composition comprising a solvent, an antiperspirant and/or deodorant ingredient, a fragrance, and an alkylated polyvinylpyrrolidone, wherein the alkylated polyvinylpyrrolidone is soluble or dispersible in the composition. The alkylated polyvinylpyrrolidone is capable of forming a film when the solvent is allowed to evaporate such that the film limits the release of the fragrance. Fragrance is released when the film is exposed to perspiration. The alkylated polyvinylpyrrolidone overcomes the problem with other film forming polymers that do not form stable films in the presence of an antiperspirant and/or deodorant ingredient.

14 Claims, No Drawings

ANTIPERSPIRANT/DEODORANT WITH ALKYLATED POLYVINYLPYRROLIDONE

BACKGROUND OF THE INVENTION

Antiperspirant and/or deodorant compositions are generally applied to an axillary region to limit perspiration and/or to limit or kill bacteria in this region. In this way, body odour caused by bacterial growth is eliminated or at least reduced.

Antiperspirants/deodorants can be delivered topically in liquid form including by roll-on, gel, or as an aerosol. When these compositions are applied to the axillary region, solvent evaporates to leave a dry coating on the skin.

A fragrance component is frequently incorporated into antiperspirant/deodorant compositions at least in part to mask body odour not eliminated by the antiperspirant/deodorant effect of the composition. Attempts have also been made to control the release of fragrances incorporated into liquid antiperspirant/deodorant compositions. It has been proposed to use an acrylate/hydroxyacrylate copolymer as a means to entrap fragrance components once applied to the skin using a roll-on or aerosol dispenser. This approach suffers from a drawback that such polymers control the release of the fragrance for only a limited period and are therefore unreliable.

There is therefore a need to provide improved antiperspirant/deodorant compositions which are more effective in controlling the release of a fragrance component thereof.

BRIEF SUMMARY OF THE INVENTION

The invention aims at least partially to meet these needs in the art.

In a first aspect, the present invention provides an antiperspirant/deodorant liquid composition comprising a solvent, an active antiperspirant or deodorant ingredient, a fragrance, and an alkylated polyvinylpyrrolidone, wherein the alkylated polyvinylpyrrolidone is soluble or dispersible in the composition. The alkylated polyvinylpyrrolidone forms a film when the solvent is allowed to evaporate such that the film limits the release of the fragrance. The film is water-soluble or water-dispersible so that the fragrance is released when the film is exposed to perspiration.

The water in the perspiration disperses or dissolves the film thereby allowing the fragrance to be released by evaporation. In this way, fragrance longevity is increased and fragrance is released when needed at a time when a subject perspires.

In a further aspect, the present invention provides use of the composition as described herein as an antiperspirant or deodorant.

In a further aspect, the present invention provides a method comprising applying a composition as described herein to the axillary area of a subject.

In a further aspect, the present invention provides a method for delivering a fragrance wherein the release rate of the fragrance increases with the perspiration rate of a subject. The method comprises topically applying the composition as described herein to the subject.

DETAILED DESCRIPTION OF THE INVENTION

The following description of the preferred embodiment(s) is merely exemplary in nature and is in no way intended to limit the invention, its application, or uses.

The solvent of the composition typically comprises water although it is possible to include co-solvents which are miscible with the water. Optionally, the solvent consists essentially of water.

The alkylated polyvinylpyrrolidone must be soluble or dispersible in water so that a film thereof is water-soluble or water-dispersible. The alkylated polyvinylpyrrolidone must also be soluble or dispersible in the composition as a whole, whether or not the solvent comprises or consists essentially of water. Alkylated polyvinylpyrrolidones according to the invention include butylated polyvinylpyrrolidones. It has been found that the alkyl polyvinylpyrrolidones of the invention are stable in the composition and do not phase separate. The composition is stable for at least 3 months, or optionally at least 6 months or more than 1 year.

In certain embodiments, the alkyl in the alkylated polyvinylpyrrolidone is $C_2$ to $C_8$. In certain embodiments, it is a butylated polyvinylpyrrolidone. The alkylated polyvinylpyrrolidone ceases to be soluble or dispersible in water and is unsuitable for use in the invention, for example, wherein the alkyl $C_{16}$ or greater, alkylated polyvinylpyrrolidones of this type are not soluble or dispersible in water and their films would be unsuitable to release fragrance in an antiperspirant/deodorant composition.

Typically, the alkylated polyvinylpyrrolidone has a molecular weight of about 16000 g/mole. The ratio of vinylpyrrolidone to alkyl groups in the alkylated polyvinylpyrrolidone is typically from 20:80 to about 90:10, more preferably about 90:10.

Antaron® and Ganex® polymers are supplied by ISP Personal Care. Butylated polyvinylpyrrolidones designated P-904LC are particularly suitable for use in the present invention.

Optionally, the composition comprises the alkylated polyvinylpyrrolidone in an amount of at least 2 wt %, preferably at least 3 wt %, more preferably at least 4 wt %, most preferably at least 5 wt %, based on the total weight of the composition. Optionally, up to 10 wt % of the alkylated polyvinylpyrrolidone may be used, preferably up to 8 wt %, more preferably up to 6 wt %, based on the total weight of the composition. In one arrangement, about 5 wt % of the alkylated polyvinylpyrrolidone may be used, based on the total weight of the composition.

The antiperspirant/deodorant composition may comprise an active antiperspirant ingredient, an active deodorant ingredient or a mixture of antiperspirant/deodorant ingredients.

Active Antiperspirant Ingredients

The active antiperspirant ingredient may be selected from aluminium salts, zirconium salts and zinc salts.

Any of the known aluminum containing antiperspirant active materials can be utilized in the composition. Antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol, aluminum-zirconium octachlorohydrate, aluminum-zirconium octachlorohydrex gly, aluminum-zirconium pentachlorohydrate, aluminum-zirconium pentachlorohydrex gly, aluminum-zirconium tetrachlorohydrate, aluminum-zirconium tetrachlorohydrex gly, aluminum-zirconium trichlorohydrate, aluminum-zirconium trichlorohydrex gly, and combinations thereof. Generally, any of the Category I active antiperspirant ingredients, listed in the Food and Drug Administration's Monograph on Antiperspirant Drug Products for over-the-counter human use (Oct. 10, 1973) can be used (21 CFR 350.10). In one embodiment, the antiperspirant active is aluminum chlorohydrate. In another embodiment, the antiperspirant active is aluminum zirconium tetrachlorhydrex propylene glycol.

In other embodiments, the antiperspirant active is an aluminum salt and/or an aluminum-zirconium salt, such as those described above, that are further stabilized by betaine and a calcium salt. More information betaine and calcium salt stabilized antiperspirant salts can be found in U.S. Patent Application Publication No. 2006/0204463 to Tang et al. In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al. In other embodiments, the type of salt of interest, an aluminum zirconium tetrasalt or octasalt free of glycine are used wherein aluminum zirconium salt is stabilized by Betaine and has a metal to chloride ratio of 0.9:1 to 1.3:1 (and in other embodiments of 0.9:1 to 1.2:1 or 0.9:1 to 1.1:1). For the tetrasalt, the Al/Zr atomic ratio can be 3.2:1 to 4.1:1.0 and the Betaine:zirconium mole ratio can be 0.2:1 to 3.0:1 (or in other embodiments of 0.4:1 to 1.5:1). Another salt that can be used is an aluminum chloride salt buffered by Betaine, wherein the salt has a metal to chloride ratio of 0.9:1 to 1.3:1 (and in other embodiments of 0.9:1 to 1.2:1 or 0.9:1 to 1.1:1). For the octasalt the Al Zr atomic ratio is 6.2:1 to 10.0:1 and the Betaine:Zr mole ratio is 0.2:1 to 3.0:1 (or in other embodiments of 0.4:1 to 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active. Additionally, the antiperspirant active can be a calcium salt stabilized antiperspirant active. Examples of calcium salt stabilized antiperspirant actives can be found in U.S. Patent Application Publication No. 2006/0204463.

Examples of commercially available glycine-free low M:C1 ratio tetrasalts and octasalts include, but are not limited to, REZAL™ AZP 955 CPG and REZAL™ AZP 885 respectively (both from SummitReheis Antiperspirant Actives of Huguenot, N.Y.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Antiperspirant actives can be incorporated into compositions in amounts of 1 to 25 weight % (on an actives basis) of the final composition, but the amount used will depend on the formulation of the composition. Generally at lower levels the antiperspirant active material will not substantially reduce the flow of perspiration as effectively, but will reduce malodor, for example, by acting also as an antimicrobial material. In certain embodiments, the base antiperspirant material can be designed to more effectively deliver the antiperspirant to the skin. In these situations, the amount of antiperspirant can be lowered but still deliver the same level of efficacy as a product with higher levels of antiperspirant. For an example of a composition that provides the same clinical efficacy at a 10 weight % antiperspirant level as other compositions that have a 17 weight % antiperspirant level, see the hydrocarbon/hydrogenated soybean oil gelled formulation in U.S. Patent Application Publication No. 2008/0187504A1. In certain embodiments, the amount of antiperspirant active is less than 12 weight %. In other embodiments, the amount of antiperspirant active is 5 to 10 weight %, 6 to 10 weight %, 7 to 10 weight %, or 8 to 10 weight %.

Optionally, the active antiperspirant ingredient is aluminium chlorohydroxide.

Active Deodorant Ingredient

In certain embodiments, the composition may include any known deodorant active. Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyltrimethylammomium bromide, cetyl pyridinium chloride, farnesol (3,7,11-trimethyl-2,6,10-dodecatrien-1-ol), N-(4-chlorophenyl)-N'-(3,4-dichlorophenyl)urea (Triclocarban), silver halides, octoxyglycerin (Sensiva™ SC 50) and various zinc salts (for example, zinc ricinoleate), bactericides, and/or bacteriostats. The deodorant active can, illustratively, be included in the composition in an amount of 0-5%, or 0.01-1% by weight, of the total weight of the composition. Triclosan can, illustratively, be included in an amount of 0.05% to 0.5% by weight, of the total weight of the composition.

Surfactant

Any surfactant that can be used in antiperspirant and/or deodorant compositions can be included. The surfactant can be included in any desired amount. In one embodiment, the amount of surfactant is about 2 to about 12% by weight of the composition. The amount in the composition is based on the as supplied material. In another embodiment, the amount of surfactant is about 3 to about 10% by weight. In one embodiment, when the composition is an oil in water roll-on formula, the amount of surfactant is about 2 to about 5%. In one embodiment, when the composition is a water in oil gel composition, the amount of surfactant is about 3 to about 10%. Examples of the surfactant include, but are not limited to, nonionic surfactants, silicone surfactants, and combinations thereof. Nonionic surfactants that can be used include, but are not limited to, (a) sorbitan esters and ethoxylated sorbitan esters (for example PEG-20 sorbitan isostearate, sorbitan monolaurate, polysorbate-20, polysorbate-40, polysorbate-60, polysorbate-80); (b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10); (c) ethoxylated adducts (for example, PEG-25 stearate, glyceryl stearate and PEG-100 stearate); (d) PEG esters (for example, PEG-8 oleate, PEG-8 laurate, PEG-8 dilaurate, PEG-12 dilaurate, PEG-80 diisostearate, PEG-40 stearate); (e) propoxylates (for example, PPG-10 butanediol, PPG-50 oleyl ether, PPG-2-ceteareth-9, PPG-3-deceth-3, PPG-5-ceteth-20); (f) ethoxylated modified triglycerides (for example, PEG-20 corn glycerides, PEG-12 palm kernel glycerides); (g) alkylphenol aromatic ethoxylates (for example, dinonylphenol ethoxylate with 9 moles of EO, octylphenol ethoxylate with 20 moles of EO, octylphenol ethoxylate with 40 moles of EO); (h) block copolymers that are alkoxylated glycols having ethoxylated and propoxylated segments (for example, POLOXAMER™ 182 and 234, POLOXAMER™ 105 Benzoate, and MEROXAPOL™ 174); and combinations thereof. In one embodiment, the nonionic surfactant is selected so that it has an HLB (hydrophilic-lipophilic balance) value of 8-16 (more particularly 8-12).

In one embodiment, the nonionic surfactant is selected from ethoxylated nonionic surfactants and propoxylated non-ionic surfactants. Example of these include, but are not limited to Steareth 2, Steareth 20, and Steareth 21. In an oil in water composition embodiment, a combination of 2 surfactants, one having an HLB value of about 2 to about 8 (such as Steareth 2) and the other having an HLB of about 9 to about 18 (such as Steareth 20 and 21), can be used.

Examples of silicone surfactants can be found in U.S. Pat. No. 6,485,716, which is incorporated herein by reference only for the listing of the silicone surfactants. Suitable silicone surfactants include silicone polyglucosides (for example, octyl dimethicone ethoxy glucoside) and silicone copolyols having an HLB value (hydrophilic lipophilic balance)<8. The HLB value may be measured in a variety of ways such as described in conventional references or found listed in tables of data recording such values. It is intended that any type of HLB measurement technique may be used.

In general, silicone copolyols include, but are not limited to, copolyols of the following Formulae I and II. Formula I materials may be represented by: $(R^{10})_3SiO[(R^{11})_2SiO]xSi(R^{12})(R^bO(C_2H_4O)_p(C_3H_6O)_sR^c)O]_ySi(R^{13})_3$ wherein each of $R^{10}$, $R^{11}$, $R^{12}$, and $R^{13}$ may be the same or different and each is chosen from C1-C6 alkyl; $R^b$ is the radical $—C_mH2_m—$; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment $—(C_2H_4O)_p—(C_3H_6O)_{\cdot s}—$ has a molecular weight in the range of 200 to 5,000; the segment preferably having fifty to one hundred mole percent of oxyethylene units $—(C_2H_4O)_p—$ and one to fifty mole percent of oxypropylene units $—(C_3H_6O)_{\cdot s}—$; x has a value of 8 to 400; and y has a value of 2 to 40. Preferably each of $R^{10}$, $R^{11}$, $R^{12}$, and $R^{13}$ is a methyl group; $R^c$ is H; m is preferably three or four whereby the group $R^b$ is most preferably the radical $—(CH_2)_3—$; and the values of p and s are such as to provide a molecular weight of the oxyalkylene segment $—(C_2H_4O)_p—(C_3H_6O)_s—$ of between about 1,000 to 3,000. In one embodiment, p and s should each have a value of about 18 to 28. In one embodiment, the silicone copolyol is dimethicone copolyol.

A second siloxane polyether (copolyol) has the Formula II: $(R^{10})_3SiO[(R^{11})_2SiO]xSi(R^{12})(R^bO(C_2H_4O)_pR^c)O]_ySi(R^{13})_3$, wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$, and $R^{13}$ substituents that are attached to the two terminal silicon atoms at the end of the siloxane chain can be substituted with the segment $—R^b—O—(C_2H_4O)_p—(C_3H_6O)_s—R^c$ or with the segment $—R^b—O—(C_2H_4O)_p—R^c$. In some instances, it may be desirable to provide the segment $—R^b—O—(C_2H_4O)_p—(C_3H_6O)_s—R^c$ or the segment $—R^b—O—(C_2H_4O)_p—R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING 5225C from Dow Corning, which is a 10% dimethicone copolyol in cyclomethicone; DOW CORNING 2-5185C, which is a 45-49% dimethicone copolyol in cyclomethicone; SILWET L-7622 from Witco; ABIL EM97 from Goldschmidt, which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING 2-5185 can be used in one embodiment.

In one embodiment, 0.5-5 weight % (particularly 1.0-2.0%) of a 10% silicone copolyol such as dimethicone copolyol in cyclomethicone mixture may be used, wherein the amount of mixture added is selected so that the level of silicone copolyol in the composition is in the range of 0.05-0.5% (particularly 0.1%) (for example, 1% of a 10% dimethicone copolyol in cyclomethicone mixture).

Gelling Agents

Gelling agents can be included in antiperspirant products that typically contain gelling agents. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

In one embodiment, the gelling agent comprises a combination of hydrogenated soybean oil and a hydrocarbon of the formula $C_nH_{2n+2}$, wherein n is 20 to 100, and the hydrocarbon is at least 90% linear. In this embodiment, the antiperspirant composition has a structure that provides a better delivery of the antiperspirant to the skin. Instead of using a typical 17 weight % level for the antiperspirant, a 10 weight % level can be used and still provide the same level of clinical wetness reduction as the 17 weight % level. By reducing the level of the antiperspirant in this embodiment, the amount of material that contributes to yellowing is reduced. This results in lower levels of yellowing.

In certain embodiments, the fully or partially hydrogenated soybean oil are those described in US2008/0187504A1 and US2008/0187503A1. The hydrogenated soybean oil from US2008/0187504A1 is almost, but not fully hydrogenated. The amount of hydrogenation is measured by the iodine value. The iodine value can be measured by ASTM D5554-95 (2006). The iodine value of the hydrogenated soybean oil used herein is greater than 0 to 20. In one embodiment, the iodine value is 1 to 5. The partially hydrogenated soybean oil from US2008/0187503A1 has a melting point that of −15° C. (5° F.) to 38° C. (100° F.). In another embodiment, the melting point is 26° C. (80° F.) to 38° C. (100° F.). To obtain the desired melting point, the oil can be partially hydrogenated or a blend of non-hydrogenated with partially or fully hydrogenated oils and/or waxes.

The partially or fully hydrogenated soybean oil is present in an amount up to 20% by weight of the composition. In another embodiment, the amount is up to 10% by weight. In one embodiment, the amount is at least 1, 2, 3, 4, 5, 6, 7, 8, or 9% by weight. In another embodiment, the amount is less than 10, 9, 8, 7, 6, 5, 4, 3, 2, 1% by weight. Any of the preceding minimum and maximum amounts can be combined to form any range of values.

The hydrocarbon is a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene/polymethylene. An example of a polyethylene can be found in U.S. Pat. No. 6,503,491. In another embodiment, the polyethylene has a weight average molecular weight of 300 to 3000 and a melting point of 50 to 129° C.

Fragrance

Any fragrance suitable for personal care use may be incorporated into the antiperspirant/deodorant compositions of the present invention. Fragrances tend to be relatively volatile aroma compounds which are capable of entering the gas phase at skin surface temperature.

Other Components

Additional components of the antiperspirant/deodorant compositions according to the invention optionally include any components suitable for use in such compositions which are known in the art. Such components include emollients, preservatives such as ditertiary butyl paracresol and quarternium15, chelators such as EDTA and other excipient materials.

The present invention also provides an antiperspirant/deodorant composition dispenser comprising a composition as described herein in a suitable container capable of dispensing the composition topically. Such containers are known in the art and include roll-on dispensers and pressurized aerosol containers.

The present invention also provides use of the composition as described herein as an antiperspirant or deodorant.

The present invention also provides a method comprising applying a composition as described herein to the axillary area of a subject.

The present invention provides a method for delivering a fragrance wherein the release rate of the fragrance increases with the perspiration rate of a subject. The method comprises topically applying the composition as described herein to the subject.

The compositions of the present invention may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use.

SPECIFIC EMBODIMENTS OF THE INVENTION

EXAMPLE 1

Evaluation of the Ability of Film-Forming Polymers to Release a Fragrance Upon Exposure to Water The ability of various film-forming water-soluble and water-dispersible polymers to release a fragrance upon exposure to water was assessed by an Odour Evaluation Board (OEB) study.

A series of fragranced AP roll-ons containing various film-forming polymers at various concentrations are prepared using standard techniques. The polymer concentrations investigated were about 5% and about 2% by weight. The concentration and nature of the fragrance is constant between solutions. A control solution which contained the fragrance alone is also prepared.

The roll-ons are applied to odourless wool swatches and allowed to dry for six hours in a 37° C., 80% relative humidity oven. Water is then applied to the substrate right before evaluation. The intensity of the fragrance released relative to a control is then assessed by an Odour Evaluation Board consisting of a panel of three expert fragrance sniffers.

TABLE 1

Film-forming polymers included in the study. All polymers investigated were water-soluble and/or water-dispersible.

| Trade Name | Manufacturer | INCI Name | Description |
|---|---|---|---|
| Dermacryl 79 | National Starch | Co-polymer | Carboxylated acrylic copolymer |
| Luviquat Ultra Care | BASF | Co-polymer | Polyquaternium 44 |
| Polymer JR | Dow | Polyquat | Polyquaternium 10 |
| HPC | Hercules | Cellulose | Hydroxypropylcellulose |
| PQ-6 100 | Nalco | Polyquat | Polyquaternium 6 |
| PQ-6 106 | Nalco | Polyquat | Polyquaternium 6 |
| Dermacryl AQF | National Starch | Co-polymer | Carboxylated acrylic copolymer |
| Luviset Clear | BASF | Co-polymer | Vinylpyrrolidone/methacrylamide/vinylimidazole copolymer |
| PVP/VA 50% solution | BASF | Co-polymer | Vinylpyrrolidone/vinylacetate copolymer |
| AllianZ LT-120 | ISP | Polymer | Acrylate/succinate/hydroxyacrylate copolymer |
| Ganex P904 LC | ISP | Polymer | Butylated polyvinylpyrrolidone |
| Luviskol K-17 | BASF | Polymer | Polyvinylpyrrolidone |
| PVP/VA E635 | ISP | Co-polymer | Vinylpyrrolidone/vinylacetate copolymer |
| Luviskol VA-73W | ISP | Polymer | Vinylpyrrolidone/vinylacetate copolymer |
| Flosoft 200 | SNF Floerger | Polymer | Methacrylate/cationic acrylamide copolymer |

Results and Discussion

Of the polymers investigated, Ganex P904, AllianZ LT-120, Dermacryl AQF and Dermacryl 79 released fragrance significantly more strongly when exposed to water in comparison to the control. Luviquat Ultra Care produced a slight to moderate effect. The remaining polymers did not produce a significant effect.

For the active polymers, the magnitude of the response to water was found to vary with the polymer concentration. For example, Ganex P904 at a concentration of 5% produced a stronger effect than Ganex P904 at a concentration of 2%. It is believed that the release of fragrances by other alkylated polyvinylpyrrolidones would show similar dose dependence.

EXAMPLE 2

Stability of High Ionic Strength Deodorant and Antiperspirant-Like Compositions Comprising Film-Forming Polymers The film-forming polymers for which a water-activated response was observed are selected for stability testing in high ionic strength media containing ingredients typical of antiperspirant and/or deodorant compositions.

Results and Discussion

AllianZ LT, Dermacryl AQF and Dermacryl 79 were found to undergo phase separation upon storage. AllianZ LT undergoes an immediate phase separation.

Dermacryl AQF and Dermacryl 79 were found to no longer produce water-sensitive release of a fragrance after storage within one day. This is believed to be a consequence of the observed phase separation.

No phase separation was observed for the compositions comprising Ganex P904. The ability of the Ganex P904 to selectively release a fragrance in response to water did not diminish after storage.

EXAMPLE 3

Gas Chromatography Headspace Testing

To further illustrate the ability of alkylated polyvinyl pyrrolidones to retain fragrance molecules, in vitro GC headspace testing is carried out.

Materials and Methods

A control antiperspirant formulation was prepared according to standard methodology. The constituents of this composition are presented in Table 2. Compositions further comprising 1% Ganex P904, 3% Ganex P904 and 5% Ganex P904 were also prepared.

TABLE 2

Control antiperspirant composition for GC headspace test

| Material | Quantity/% |
| --- | --- |
| Steareth-20 | 1.14 |
| Polypropylene glycol-15 stearyl ether | 1.49 |
| Steareth-2 | 2.19 |
| Hydrogenated Soybean Oil | 2.86 |
| 50% Aluminium chlorhydroxide low molecular weight solution | 28.6 |
| Demineralized water and minors | Q.S. |

A sample of 0.30±0.01 gram of each composition is evenly spread on a 1"×2" (2.54 cm ×5.08 cm) wool swatch. The swatches are then placed in an incubator at 37° C. and 80% relative humidity for 6 hours. The swatches are then removed from the incubator and loaded into sealed sample vials before being transferred to the gas chromatograph. The samples are equilibrated at 50° C. for 1 hour. A sample of the headspace gas is then extracted by an autosampler and gas chromatography carried out. The integral of the fragrance peak in the resulting chromatogram corresponds to the intensity of the fragrance. All measurements are performed in triplicate and the results averaged.

Results and Discussion

The average fragrance intensities recorded are set out in the Table 3, below.

TABLE 3

Results of GC headspace analysis

| | Fragrance intensity | St. dev |
| --- | --- | --- |
| Control (roll-on) | 44959 | 8388 |
| Roll-on with 1% Ganex P904 | 48259 | 4567 |
| Roll-on with 3% Ganex P904 | 72341 | 8996 |
| Roll-on with 5% Ganex P904 | 81134 | 5605 |

The data shows that compositions comprising 5% Ganex P904 and 3% Ganex P904 produce a significant increase in fragrance intensity. A lower effect is observed at 1% alkylated polyvinyl pyrrolidone.

EXAMPLE 4

Panel Study

An in vivo assessment of the performance of an antiperspirant composition comprising alkylated polyvinyl pyrrolidone relative to a control is performed. The composition comprising alkylated polyvinyl pyrrolidone is found to produce a statistically significant increase in fragrance release compared to the control when perspiration is induced.

Materials and Methods

A control formulation and a formulation comprising an alkylated polyvinyl pyrrolidone are applied to 15 volunteers. After a period of 6 hours following the application of the compositions, the volunteers spent 15 minutes in a hot room. The room is at a temperature of 40.5° C. (105° F.) and 40% relative humidity. Throughout the study, the volunteers carry out self-evaluations of the strength of the fragrance of the deodorant compositions at 5 minute intervals. A rating scale of 0 to 7 is used, wherein 0 corresponds to no scent and 7 corresponds to a very strong scent.

Results and Discussion

During the first 6 hours after the sample application, before entering the hot room, the two samples showed no significant difference in fragrance intensity. In the conditions of the hot room, the composition comprising alkylated polyvinyl pyrrolidone was found to give a more intense fragrance than the control, as shown in Table 4. This indicates that deodorant comprising alkylated polyvinyl pyrrolidones provide for a sweat activated fragrance release.

TABLE 4 results of panel test during hot room phase

| | 10 min (hot room) | | 15 min (hot room) | |
| --- | --- | --- | --- | --- |
| | Rating | p value | Rating | p value |
| Control | 1.87 | | 1.93 | |
| Ganex P904 | 2.53 | 0.01 | 2.33 | 0.05 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

We claim:

1. An antiperspirant /deodorant liquid composition, comprising:
   a solvent in a sufficient amount to form a liquid composition,
   an antiperspirant and/or deodorant ingredient,
   a fragrance, an alkylated polyvinylpyrrolidone solubilized or dispersed throughout the liquid composition, wherein the alkylated polyvinylpyrrolidone is a $C_2$ to $C_8$ alkylated polyvinylpyrrolidone, a surfactant, and a gellant, wherein the alkylated polyvinylpyrrolidone is present in an amount of at least 2 wt % based on the total weight of the liquid composition, and wherein the solvent consists of water.

2. The composition of claim 1 wherein the alkylated polyvinylpyrrolidone is butylated polyvinylpyrrolidone.

3. The composition of claim 1 wherein the alkylated polyvinylpyrrolidone has a molecular weight of about 16000.

4. The composition of claim 1 wherein a ratio of vinylpyrrolidone groups to alkyl groups in the alkylated polyvinylpyrrolidone is from 20:80 to 90:10.

5. The composition of claim 1 wherein a ratio of vinylpyrrolidone groups to alkyl groups is about 90:10.

6. The composition of claim 1 wherein the antiperspirant and/or deodorant ingredient is an antiperspirant ingredient.

7. The composition of claim 6 wherein the antiperspirant ingredient is selected from aluminium salts and aluminium-zirconium salts.

8. The composition of claim 7 wherein the antiperspirant ingredient is an aluminium chlorohydrate.

9. The composition of claim 1, wherein the surfactant is present in an amount of 2 to 12% by weight, based on the total weight of the liquid composition.

10. The composition of claim 1, wherein the gellant is present in an amount of up to 20% by weight, based on the total weight of the liquid composition.

11. The composition of claim 1, wherein the gellant comprises hydrogenated vegetable oil.

12. The composition of claim 1, wherein the alkylated polyvinylpyrrolidone solubilized or dispersed throughout the liquid composition forms a stable film in the presence of the antiperspirant and/or deodorant ingredient, upon evaporation of the solvent from the liquid composition, and wherein the stable film limits the release of the fragrance.

13. The composition of claim 1, wherein the liquid composition is an oil in water roll-on formula and wherein the surfactant is present in an amount of 2 to 5% by weight, based on the total weight of the liquid composition.

14. The composition of claim 1, wherein the liquid composition is a water in oil gel composition and wherein the surfactant is present in an amount of 3 to 10% by weight, based on the total weight of the liquid composition.

* * * * *